United States Patent
Chang et al.

(10) Patent No.: US 7,049,122 B2
(45) Date of Patent: May 23, 2006

(54) MUTANT-TYPE LIPASES AND APPLICATIONS THEREOF

(75) Inventors: Rey-Chang Chang, Kaohsiung (TW); Shu-Jen Chou, Taipei (TW); Jei-Fu Shaw, Taipei (TW)

(73) Assignee: Academia Sinica, Taipei (TW)

( * ) Notice: Subject to any disclaimer, the term of this patent is extended or adjusted under 35 U.S.C. 154(b) by 560 days.

(21) Appl. No.: 10/233,443

(22) Filed: Sep. 4, 2002

(65) Prior Publication Data

US 2003/0109019 A1 Jun. 12, 2003

Related U.S. Application Data

(60) Provisional application No. 60/323,704, filed on Sep. 21, 2001.

(51) Int. Cl.
*C12N 9/20* (2006.01)
(52) U.S. Cl. .................. 435/198; 435/197; 435/196; 435/440; 435/135; 426/533
(58) Field of Classification Search ............. 435/195, 435/196, 197; 536/23.2
See application file for complete search history.

(56) References Cited

OTHER PUBLICATIONS

Wallace, A. et al.; Derivation of 3D coordinate templates for searching structural databases: Application to Ser-His-Asp catalytic triads in the serine proteinases and lipases; Protein Science, vol. 5, p. 1001-1013, (1996).
Sharrocks, A. et al.; Improved primer design for PCR-based, site-directed mutagenesis; Nucleic Acids Research, vol. 20, No. 5, p. 1147, (1992).
Chang, R. et al.; Synthesis of Fatty Acid Esters by Recombinant *Staphylococcus epidermidis* Lipases in Aqueous Environment; Journal of Agricultural and Food Chemistry, vol. 49, No. 5, p. 2619-2622, (2001).
Chang, R. et al.; Site-Directed Mutagenesis of a Highly Active *Staphylococcus epidermidis* Lipases Fragment Identifies Residues Essential for Catalysis; Journal of American Oil Chemists' Society, vol. 77, No. 10, p. 1021-1025, (2000).
Simons, J. et al.; Cloning, purification and charaterisation of the lipase from *Staphylococcus epidermidis*—Comparison of the substrate selectivity with those of other microbial lipases; Eur. J. Biochem, vol. 253, p. 675-683, (1998).
Farrell, A. et al.; Molecular analysis and expression of the lipase of *Staphylococcus epidermidis*; Journal of General Microbiology, vol. 139, p. 267-277, (1993).
Talon, R. et al.; Production of flavor esters by lipases of *Staphylococcus warneri* and *Staphylococcus xylosus*; Enzyme and Microbial Technology, vol. 19, p. 620-622, (1996).

*Primary Examiner*—Nashaat T. Nashed
(74) *Attorney, Agent, or Firm*—Fei-Fei Chao; Bingham McCutchen LLP (57) ABSTRACT

The present invention provides mutant-type lipases which demonstrate superior lipolytic and esterific activities. The mutant-type lipases are characterized by an amino acid alteration at the residue immediately followed either the serine residue or the histidine residue or both residues of the Ser-His-Asp catalytic triad. The Ser-His-Asp catalytic triad is known to be the three residues, although occur far apart in the amino acid sequence of a lipase, that contribute to the hydrolytic activity in the active site of the lipase. The amino acid residue that follows the serine residue of the Ser-His-Asp catalytic triad is alanine. The amino acid residue that follows the histidine residue of the Ser-His-Asp catalytic triad is isoleucine. The wild-type lipase is preferably originated from *Staphylococcus*, particularly *Staphylococcus epidermindis*. The present invention also relates to a method for preparing the mutant-type lipases by site-directed mutagenesis using PCR and a method for utilizing the mutant-type lipase to catalyze synthesis of flavor esters to be used in food industry.

28 Claims, 1 Drawing Sheet

Figure 1

SEQUENCE LISTING

<160> NUMBER OF SEQ ID NOS: 17

<210> SEQ ID NO 1
<211> LENGTH: 30
<212> TYPE: DNA
<213> ORGANISM: Artificial Sequence
<220> FEATURE:
<223> OTHER INFORMATION: designed nucleotide to act as the N-terminal
      primer for selection of S. epidermidis strain 9 lipase

<400> SEQUENCE: 1
ggggccatgg aacaaaaaca atataaaaat                                     30

<210> SEQ ID NO 2
<211> LENGTH: 31
<212> TYPE: DNA
<213> ORGANISM: artificial sequence
<220> FEATURE:
<223> OTHER INFORMATION: designed nucleotide to act as the C-terminal
      primer for selection of S. epidermidis strain 9 lipase

<400> SEQUENCE: 2
ggggctcgag tttatttgtt gatgttaatt g                                   31

<210> SEQ ID NO 3
<211> LENGTH: 22
<212> TYPE: DNA
<213> ORGANISM: Artificial Sequence
<220> FEATURE:
<223> OTHER INFORMATION: designed nucleotide to act as the primer for
      selection of wild-type S. epidermidis strain 9 lipase with Ser418

<400> SEQUENCE: 3
gaccacccat actatgacca ac                                             22

<210> SEQ ID NO 4
<211> LENGTH: 18
<212> TYPE: DNA
<213> ORGANISM: Artificial Sequence
<220> FEATURE:
<223> OTHER INFORMATION: designed nucleotide to act as the primer for
      selection of S. epidermidis strain 9 lipase with S418C side-
      directed mutation

<400> SEQUENCE: 4
acccatacaa tgaccaac                                                  18

<210> SEQ ID NO 5
<211> LENGTH: 22
<212> TYPE: DNA
<213> ORGANISM: Artificial Sequence
<220> FEATURE:
<223> OTHER INFORMATION: designed nucleotide to act as the primer for
      selection of S. epidermidis strain 9 lipase with M419L side-
      directed mutation

<400> SEQUENCE: 5
gaccaccgag actatgacca ac                                             22

<210> SEQ ID NO 6
<211> LENGTH: 22
<212> TYPE: DNA
<213> ORGANISM: Artificial Sequence
<220> FEATURE:
<223> OTHER INFORMATION: designed nucleotide to act as the primer for
      selection of S. epidermidis strain 9 lipase with M419A side- -continued directed mutation

<400> SEQUENCE: 6
gaccaccggc actatgacca ac          22

<210> SEQ ID NO 7
<211> LENGTH: 22
<212> TYPE: DNA
<213> ORGANISM: Artificial Sequence
<220> FEATURE:
<223> OTHER INFORMATION: designed nucleotide to act as the primer for
      selection of S. epidermidis strain 9 lipase with M419Q side-
      directed mutation

<400> SEQUENCE: 7
gaccaccttg actatgacca ac          22

<210> SEQ ID NO 8
<211> LENGTH: 22
<212> TYPE: DNA
<213> ORGANISM: Artificial Sequence
<220> FEATURE:
<223> OTHER INFORMATION: designed nucleotide to act as the primer for
      selection of wild-type S. epidermidis strain 9 lipase with H648

<400> SEQUENCE: 8
gggatcatgt agactttgta gg          22

<210> SEQ ID NO 9
<211> LENGTH: 18
<212> TYPE: DNA
<213> ORGANISM: Artificial Sequence
<220> FEATURE:
<223> OTHER INFORMATION: designed nucleotide to act as the primer for
      selection of S. epidermidis strain 9 lipase with H648K side-
      directed mutation

<400> SEQUENCE: 9
tgggataaag tagacttt          18

<210> SEQ ID NO 10
<211> LENGTH: 22
<212> TYPE: DNA
<213> ORGANISM: Artificial Sequence
<220> FEATURE:
<223> OTHER INFORMATION: designed nucleotide to act as the primer for
      selection of S. epidermidis strain 9 lipase with V649L side-
      directed mutation

<400> SEQUENCE: 10
gggatcatct cgactttgta gg          22

<210> SEQ ID NO 11
<211> LENGTH: 22
<212> TYPE: DNA
<213> ORGANISM: Artificial Sequence
<220> FEATURE:
<223> OTHER INFORMATION: designed nucleotide to act as the primer for
      selection of S. epidermidis strain 9 lipase with V649I side-
      directed mutation

<400> SEQUENCE: 11
gggatcatat cgactttgta gg          22

<210> SEQ ID NO 12
<211> LENGTH: 22
<212> TYPE: DNA

```
<213> ORGANISM: Artificial Sequence
<220> FEATURE:
<223> OTHER INFORMATION: designed nucleotide to act as the primer for
      selection of S. epidermidis strain 9 lipase with V649A side-
      directed mutation

<400> SEQUENCE: 12
gggatcatgc tgactttgta gg                                              22

<210> SEQ ID NO 13
<211> LENGTH: 1158
<212> TYPE: DNA
<213> ORGANISM: Staphylococcus epidermidis
<220> FEATURE:
<221> NAME/KEY: CDS
<222> LOCATION: (1)..(1158)
<223> OTHER INFORMATION:

<400> SEQUENCE: 13
```

| | | | | | | | | | | | | | | | | |
|---|---|---|---|---|---|---|---|---|---|---|---|---|---|---|---|---|
| aaa | caa | aaa | caa | tat | aaa | aat | aat | gat | cca | att | att | tta | gta | cat | ggt | 48 |
| Lys | Gln | Lys | Gln | Tyr | Lys | Asn | Asn | Asp | Pro | Ile | Ile | Leu | Val | His | Gly | |
| 1 | | | | 5 | | | | | 10 | | | | | 15 | | |
| ttc | aat | gga | ttt | aca | gac | gat | atc | aac | cca | tca | gtg | cta | acg | cat | tat | 96 |
| Phe | Asn | Gly | Phe | Thr | Asp | Asp | Ile | Asn | Pro | Ser | Val | Leu | Thr | His | Tyr | |
| | | | 20 | | | | | 25 | | | | | 30 | | | |
| tgg | ggt | ggc | gat | aaa | atg | aat | att | cgc | caa | gat | ttg | gaa | gaa | aat | gga | 144 |
| Trp | Gly | Gly | Asp | Lys | Met | Asn | Ile | Arg | Gln | Asp | Leu | Glu | Glu | Asn | Gly | |
| | | 35 | | | | | 40 | | | | | 45 | | | | |
| tat | gag | gct | tat | gaa | gca | agt | ata | agt | gca | ttt | ggt | agt | aac | tat | gac | 192 |
| Tyr | Glu | Ala | Tyr | Glu | Ala | Ser | Ile | Ser | Ala | Phe | Gly | Ser | Asn | Tyr | Asp | |
| 50 | | | | | 55 | | | | | 60 | | | | | | |
| cgt | gct | gtt | gag | tta | tac | tac | tac | atc | aaa | ggt | gga | cgt | gtt | gac | tat | 240 |
| Arg | Ala | Val | Glu | Leu | Tyr | Tyr | Tyr | Ile | Lys | Gly | Gly | Arg | Val | Asp | Tyr | |
| 65 | | | | 70 | | | | | 75 | | | | | 80 | | |
| ggt | gca | gca | cac | gca | gct | aaa | tat | ggt | cat | gag | cgt | tac | ggt | aaa | acc | 288 |
| Gly | Ala | Ala | His | Ala | Ala | Lys | Tyr | Gly | His | Glu | Arg | Tyr | Gly | Lys | Thr | |
| | | | | 85 | | | | | 90 | | | | | 95 | | |
| tat | gaa | ggt | gtt | tat | aaa | gat | tgg | aaa | cca | ggt | caa | aaa | ata | cat | tta | 336 |
| Tyr | Glu | Gly | Val | Tyr | Lys | Asp | Trp | Lys | Pro | Gly | Gln | Lys | Ile | His | Leu | |
| | | | 100 | | | | | 105 | | | | | 110 | | | |
| gtt | ggt | cat | agt | atg | ggt | ggt | caa | aca | att | cgt | caa | tta | gaa | gag | cta | 384 |
| Val | Gly | His | Ser | Met | Gly | Gly | Gln | Thr | Ile | Arg | Gln | Leu | Glu | Glu | Leu | |
| | | 115 | | | | | 120 | | | | | 125 | | | | |
| ttg | aga | cat | ggt | aat | cca | gaa | gaa | gtt | gaa | tat | caa | aaa | caa | cat | ggt | 432 |
| Leu | Arg | His | Gly | Asn | Pro | Glu | Glu | Val | Glu | Tyr | Gln | Lys | Gln | His | Gly | |
| 130 | | | | | 135 | | | | | 140 | | | | | | |
| ggg | gaa | att | tct | cca | tta | tac | caa | ggt | ggc | cac | gac | aat | atg | gtg | tca | 480 |
| Gly | Glu | Ile | Ser | Pro | Leu | Tyr | Gln | Gly | Gly | His | Asp | Asn | Met | Val | Ser | |
| 145 | | | | 150 | | | | | 155 | | | | | 160 | | |
| tct | att | aca | aca | ctc | ggt | aca | cca | cat | aat | ggt | aca | cat | gcc | tca | gac | 528 |
| Ser | Ile | Thr | Thr | Leu | Gly | Thr | Pro | His | Asn | Gly | Thr | His | Ala | Ser | Asp | |
| | | | | 165 | | | | | 170 | | | | | 175 | | |
| tta | tta | ggt | aac | gaa | gcc | att | gta | cgc | caa | ctt | gca | tat | gac | gta | ggt | 576 |
| Leu | Leu | Gly | Asn | Glu | Ala | Ile | Val | Arg | Gln | Leu | Ala | Tyr | Asp | Val | Gly | |
| | | | 180 | | | | | 185 | | | | | 190 | | | |
| aaa | atg | tat | ggt | aat | aaa | gat | tca | cgt | gta | gac | ttt | ggg | tta | gaa | cac | 624 |
| Lys | Met | Tyr | Gly | Asn | Lys | Asp | Ser | Arg | Val | Asp | Phe | Gly | Leu | Glu | His | |
| | | | | 195 | | | | | 200 | | | | | 205 | | |
| tgg | gga | tta | aaa | caa | aaa | cca | aac | gaa | tca | tat | att | caa | tat | gtt | aaa | 672 |
| Trp | Gly | Leu | Lys | Gln | Lys | Pro | Asn | Glu | Ser | Tyr | Ile | Gln | Tyr | Val | Lys | |
| | | 210 | | | | | 215 | | | | | 220 | | | | |
| cgt | gtt | caa | aat | tca | aaa | ctg | tgg | aaa | tca | aaa | gat | agt | ggt | tta | cac | 720 |

-continued

```
Arg Val Gln Asn Ser Lys Leu Trp Lys Ser Lys Asp Ser Gly Leu His
225                 230                 235                 240 gat tta aca cgc gat ggc gca aca gat tta aac cga aaa aca tca tta    768
Asp Leu Thr Arg Asp Gly Ala Thr Asp Leu Asn Arg Lys Thr Ser Leu
                245                 250                 255 aat cct aat att gta tat aaa act tat act ggc gag tca aca cat aaa    816
Asn Pro Asn Ile Val Tyr Lys Thr Tyr Thr Gly Glu Ser Thr His Lys
            260                 265                 270 aca ttg gca gga aaa caa aaa gct gat ctt aac atg ttc tta cca ttt    864
Thr Leu Ala Gly Lys Gln Lys Ala Asp Leu Asn Met Phe Leu Pro Phe
        275                 280                 285 aca att act ggt aat tta att gga aaa gct aaa gag aaa gaa tgg aga    912
Thr Ile Thr Gly Asn Leu Ile Gly Lys Ala Lys Glu Lys Glu Trp Arg
    290                 295                 300 gaa aat gat gga ctt gtt tca gtc att tct tca caa cat cca ttt aat    960
Glu Asn Asp Gly Leu Val Ser Val Ile Ser Ser Gln His Pro Phe Asn
305                 310                 315                 320 caa aaa tat gtt gaa gct aca gat aaa aat caa aaa ggt gta tgg caa   1008
Gln Lys Tyr Val Glu Ala Thr Asp Lys Asn Gln Lys Gly Val Trp Gln
                325                 330                 335 gta act cca aca aaa cat gac tgg gat cat gta gac ttt gta ggc caa   1056
Val Thr Pro Thr Lys His Asp Trp Asp His Val Asp Phe Val Gly Gln
            340                 345                 350 gac agt aca gat aca aaa cgt act aga gat gaa ttg caa cag ttc tgg   1104
Asp Ser Thr Asp Thr Lys Arg Thr Arg Asp Glu Leu Gln Gln Phe Trp
        355                 360                 365 cat ggt ctt gct gaa gat tta gta caa agt gaa caa tta aca tca aca   1152
His Gly Leu Ala Glu Asp Leu Val Gln Ser Glu Gln Leu Thr Ser Thr
    370                 375                 380 aat aaa                                                            1158
Asn Lys
385
```

```
<210> SEQ ID NO 14
<211> LENGTH: 386
<212> TYPE: PRT
<213> ORGANISM: Staphylococcus epidermidis

<400> SEQUENCE: 14

Lys Gln Lys Gln Tyr Lys Asn Asn Asp Pro Ile Ile Leu Val His Gly
1               5                   10                  15

Phe Asn Gly Phe Thr Asp Asp Ile Asn Pro Ser Val Leu Thr His Tyr
            20                  25                  30

Trp Gly Gly Asp Lys Met Asn Ile Arg Gln Asp Leu Glu Glu Asn Gly
        35                  40                  45

Tyr Glu Ala Tyr Glu Ala Ser Ile Ser Ala Phe Gly Ser Asn Tyr Asp
    50                  55                  60

Arg Ala Val Glu Leu Tyr Tyr Tyr Ile Lys Gly Gly Arg Val Asp Tyr
65                  70                  75                  80

Gly Ala Ala His Ala Ala Lys Tyr Gly His Glu Arg Tyr Gly Lys Thr
                85                  90                  95

Tyr Glu Gly Val Tyr Lys Asp Trp Pro Gly Gln Lys Ile His Leu
            100                 105                 110

Val Gly His Ser Met Gly Gly Gln Thr Ile Arg Gln Leu Glu Glu Leu
        115                 120                 125

Leu Arg His Gly Asn Pro Glu Glu Val Glu Tyr Gln Lys Gln His Gly
    130                 135                 140

Gly Glu Ile Ser Pro Leu Tyr Gln Gly Gly His Asp Asn Met Val Ser
```

-continued

```
                145                 150                 155                 160
Ser Ile Thr Thr Leu Gly Thr Pro His Asn Gly Thr His Ala Ser Asp
                    165                 170                 175

Leu Leu Gly Asn Glu Ala Ile Val Arg Gln Leu Ala Tyr Asp Val Gly
                180                 185                 190

Lys Met Tyr Gly Asn Lys Asp Ser Arg Val Asp Phe Gly Leu Glu His
            195                 200                 205

Trp Gly Leu Lys Gln Lys Pro Asn Glu Ser Tyr Ile Gln Tyr Val Lys
        210                 215                 220

Arg Val Gln Asn Ser Lys Leu Trp Lys Ser Lys Asp Ser Gly Leu His
225                 230                 235                 240

Asp Leu Thr Arg Asp Gly Ala Thr Asp Leu Asn Arg Lys Thr Ser Leu
                245                 250                 255

Asn Pro Asn Ile Val Tyr Lys Thr Tyr Thr Gly Glu Ser Thr His Lys
                260                 265                 270

Thr Leu Ala Gly Lys Gln Lys Ala Asp Leu Asn Met Phe Leu Pro Phe
            275                 280                 285

Thr Ile Thr Gly Asn Leu Ile Gly Lys Ala Lys Glu Lys Glu Trp Arg
        290                 295                 300

Glu Asn Asp Gly Leu Val Ser Val Ile Ser Ser Gln His Pro Phe Asn
305                 310                 315                 320

Gln Lys Tyr Val Glu Ala Thr Asp Lys Asn Gln Lys Gly Val Trp Gln
                325                 330                 335

Val Thr Pro Thr Lys His Asp Trp Asp His Val Asp Phe Val Gly Gln
                340                 345                 350

Asp Ser Thr Asp Thr Lys Arg Thr Arg Asp Glu Leu Gln Gln Phe Trp
            355                 360                 365

His Gly Leu Ala Glu Asp Leu Val Gln Ser Glu Gln Leu Thr Ser Thr
        370                 375                 380

Asn Lys
385

<210> SEQ ID NO 15
<211> LENGTH: 386
<212> TYPE: PRT
<213> ORGANISM: Artificial Sequence
<220> FEATURE:
<223> OTHER INFORMATION: Amino acid sequence of the S. epidermidis
      strain 9 lipase with M419A side-direction mutation

<400> SEQUENCE: 15

Lys Gln Lys Gln Tyr Lys Asn Asn Asp Pro Ile Ile Leu Val His Gly
1               5                   10                  15

Phe Asn Gly Phe Thr Asp Asp Ile Asn Pro Ser Val Leu Thr His Tyr
                20                  25                  30

Trp Gly Gly Asp Lys Met Asn Ile Arg Gln Asp Leu Glu Glu Asn Gly
            35                  40                  45

Tyr Glu Ala Tyr Glu Ala Ser Ile Ser Ala Phe Gly Ser Asn Tyr Asp
        50                  55                  60

Arg Ala Val Glu Leu Tyr Tyr Ile Lys Gly Gly Arg Val Asp Tyr
65                  70                  75                  80

Gly Ala Ala His Ala Ala Lys Tyr Gly His Glu Arg Tyr Gly Lys Thr
                85                  90                  95

Tyr Glu Gly Val Tyr Lys Asp Trp Lys Pro Gly Gln Lys Ile His Leu
            100                 105                 110
```

-continued

```
Val Gly His Ser Ala Gly Gly Gln Thr Ile Arg Gln Leu Glu Glu Leu
        115                 120                 125

Leu Arg His Gly Asn Pro Glu Val Glu Tyr Gln Lys Gln His Gly
    130                 135                 140

Gly Glu Ile Ser Pro Leu Tyr Gln Gly Gly His Asp Asn Met Val Ser
145                 150                 155                 160

Ser Ile Thr Thr Leu Gly Thr Pro His Asn Gly Thr His Ala Ser Asp
                165                 170                 175

Leu Leu Gly Asn Glu Ala Ile Val Arg Gln Leu Ala Tyr Asp Val Gly
            180                 185                 190

Lys Met Tyr Gly Asn Lys Asp Ser Arg Val Asp Phe Gly Leu Glu His
        195                 200                 205

Trp Gly Leu Lys Gln Lys Pro Asn Glu Ser Tyr Ile Gln Tyr Val Lys
    210                 215                 220

Arg Val Gln Asn Ser Lys Leu Trp Lys Ser Lys Asp Ser Gly Leu His
225                 230                 235                 240

Asp Leu Thr Arg Asp Gly Ala Thr Asp Leu Asn Arg Lys Thr Ser Leu
                245                 250                 255

Asn Pro Asn Ile Val Tyr Lys Thr Tyr Thr Gly Glu Ser Thr His Lys
            260                 265                 270

Thr Leu Ala Gly Lys Gln Lys Ala Asp Leu Asn Met Phe Leu Pro Phe
        275                 280                 285

Thr Ile Thr Gly Asn Leu Ile Gly Lys Ala Lys Glu Lys Glu Trp Arg
    290                 295                 300

Glu Asn Asp Gly Leu Val Ser Val Ile Ser Ser Gln His Pro Phe Asn
305                 310                 315                 320

Gln Lys Tyr Val Glu Ala Thr Asp Lys Asn Gln Lys Gly Val Trp Gln
                325                 330                 335

Val Thr Pro Thr Lys His Asp Trp Asp His Val Asp Phe Val Gly Gln
            340                 345                 350

Asp Ser Thr Asp Thr Lys Arg Thr Arg Asp Glu Leu Gln Gln Phe Trp
        355                 360                 365

His Gly Leu Ala Glu Asp Leu Val Gln Ser Glu Gln Leu Thr Ser Thr
    370                 375                 380

Asn Lys
385
```

<210> SEQ ID NO 16
<211> LENGTH: 386
<212> TYPE: PRT
<213> ORGANISM: Artificial Sequence
<220> FEATURE:
<223> OTHER INFORMATION: Amino acid sequence of the S. epidermidis
    strain 9 lipase with H648K side-direction mutation

<400> SEQUENCE: 16

```
Lys Gln Lys Gln Tyr Lys Asn Asn Asp Pro Ile Ile Leu Val His Gly
1               5                   10                  15

Phe Asn Gly Phe Thr Asp Asp Ile Asn Pro Ser Val Leu Thr His Tyr
            20                  25                  30

Trp Gly Gly Asp Lys Met Asn Ile Arg Gln Asp Leu Glu Glu Asn Gly
        35                  40                  45

Tyr Glu Ala Tyr Glu Ala Ser Ile Ser Ala Phe Gly Ser Asn Tyr Asp
    50                  55                  60

Arg Ala Val Glu Leu Tyr Tyr Tyr Ile Lys Gly Gly Arg Val Asp Tyr
65                  70                  75                  80
```

```
Gly Ala Ala His Ala Ala Lys Tyr Gly His Glu Arg Tyr Gly Lys Thr
                85                  90                  95

Tyr Glu Gly Val Tyr Lys Asp Trp Lys Pro Gly Gln Lys Ile His Leu
            100                 105                 110

Val Gly His Ser Met Gly Gly Gln Thr Ile Arg Gln Leu Glu Glu Leu
        115                 120                 125

Leu Arg His Gly Asn Pro Glu Glu Val Glu Tyr Gln Lys Gln His Gly
    130                 135                 140

Gly Glu Ile Ser Pro Leu Tyr Gln Gly Gly His Asp Asn Met Val Ser
145                 150                 155                 160

Ser Ile Thr Thr Leu Gly Thr Pro His Asn Gly Thr His Ala Ser Asp
                165                 170                 175

Leu Leu Gly Asn Glu Ala Ile Val Arg Gln Leu Ala Tyr Asp Val Gly
            180                 185                 190

Lys Met Tyr Gly Asn Lys Asp Ser Arg Val Asp Phe Gly Leu Glu His
        195                 200                 205

Trp Gly Leu Lys Gln Lys Pro Asn Glu Ser Tyr Ile Gln Tyr Val Lys
    210                 215                 220

Arg Val Gln Asn Ser Lys Leu Trp Lys Ser Lys Asp Ser Gly Leu His
225                 230                 235                 240

Asp Leu Thr Arg Asp Gly Ala Thr Asp Leu Asn Arg Lys Thr Ser Leu
                245                 250                 255

Asn Pro Asn Ile Val Tyr Lys Thr Tyr Thr Gly Glu Ser Thr His Lys
            260                 265                 270

Thr Leu Ala Gly Lys Gln Lys Ala Asp Leu Asn Met Phe Leu Pro Phe
        275                 280                 285

Thr Ile Thr Gly Asn Leu Ile Gly Lys Ala Lys Glu Lys Glu Trp Arg
    290                 295                 300

Glu Asn Asp Gly Leu Val Ser Val Ile Ser Ser Gln His Pro Phe Asn
305                 310                 315                 320

Gln Lys Tyr Val Glu Ala Thr Asp Lys Asn Gln Lys Gly Val Trp Gln
                325                 330                 335

Val Thr Pro Thr Lys His Asp Trp Asp Lys Val Asp Phe Val Gly Gln
            340                 345                 350

Asp Ser Thr Asp Thr Lys Arg Thr Arg Asp Glu Leu Gln Gln Phe Trp
        355                 360                 365

His Gly Leu Ala Glu Asp Leu Val Gln Ser Gln Leu Thr Ser Thr
    370                 375                 380

Asn Lys
385

<210> SEQ ID NO 17
<211> LENGTH: 386
<212> TYPE: PRT
<213> ORGANISM: Artificial Sequence
<220> FEATURE:
<223> OTHER INFORMATION: Amino acid sequence of the S. epidermidis
      strain 9 lipase with V649I side-direction mutation

<400> SEQUENCE: 17

Lys Gln Lys Gln Tyr Lys Asn Asn Asp Pro Ile Ile Leu Val His Gly
1               5                   10                  15

Phe Asn Gly Phe Thr Asp Asp Ile Asn Pro Ser Val Leu Thr His Tyr
            20                  25                  30

Trp Gly Gly Asp Lys Met Asn Ile Arg Gln Asp Leu Glu Glu Asn Gly
```

-continued

```
                35                  40                  45
Tyr Glu Ala Tyr Glu Ala Ser Ile Ser Ala Phe Gly Ser Asn Tyr Asp
 50                  55                  60

Arg Ala Val Glu Leu Tyr Tyr Ile Lys Gly Arg Val Asp Tyr
 65                  70                  75                  80

Gly Ala Ala His Ala Ala Lys Tyr Gly His Glu Arg Tyr Gly Lys Thr
                 85                  90                  95

Tyr Glu Gly Val Tyr Lys Asp Trp Lys Pro Gly Gln Lys Ile His Leu
                100                 105                 110

Val Gly His Ser Met Gly Gly Gln Thr Ile Arg Gln Leu Glu Glu Leu
                115                 120                 125

Leu Arg His Gly Asn Pro Glu Glu Val Glu Tyr Gln Lys Gln His Gly
                130                 135                 140

Gly Glu Ile Ser Pro Leu Tyr Gln Gly Gly His Asp Asn Met Val Ser
145                 150                 155                 160

Ser Ile Thr Thr Leu Gly Thr Pro His Asn Gly Thr His Ala Ser Asp
                165                 170                 175

Leu Leu Gly Asn Glu Ala Ile Val Arg Gln Leu Ala Tyr Asp Val Gly
                180                 185                 190

Lys Met Tyr Gly Asn Lys Asp Ser Arg Val Asp Phe Gly Leu Glu His
                195                 200                 205

Trp Gly Leu Lys Gln Lys Pro Asn Glu Ser Tyr Ile Gln Tyr Val Lys
                210                 215                 220

Arg Val Gln Asn Ser Lys Leu Trp Lys Ser Lys Asp Ser Gly Leu His
225                 230                 235                 240

Asp Leu Thr Arg Asp Gly Ala Thr Asp Leu Asn Arg Lys Thr Ser Leu
                245                 250                 255

Asn Pro Asn Ile Val Tyr Lys Thr Tyr Thr Gly Glu Ser Thr His Lys
                260                 265                 270

Thr Leu Ala Gly Lys Gln Lys Ala Asp Leu Asn Met Phe Leu Pro Phe
                275                 280                 285

Thr Ile Thr Gly Asn Leu Ile Gly Lys Ala Lys Glu Lys Glu Trp Arg
                290                 295                 300

Glu Asn Asp Gly Leu Val Ser Val Ile Ser Ser Gln His Pro Phe Asn
305                 310                 315                 320

Gln Lys Tyr Val Glu Ala Thr Asp Lys Asn Gln Lys Gly Val Trp Gln
                325                 330                 335

Val Thr Pro Thr Lys His Asp Trp Asp His Ile Asp Phe Val Gly Gln
                340                 345                 350

Asp Ser Thr Asp Thr Lys Arg Thr Arg Asp Glu Leu Gln Gln Phe Trp
                355                 360                 365

His Gly Leu Ala Glu Asp Leu Val Gln Ser Glu Gln Leu Thr Ser Thr
                370                 375                 380

Asn Lys
385
```

MUTANT-TYPE LIPASES AND APPLICATIONS THEREOF

RELATED APPLICATION

This application claims the priority of U.S. Provisional Patent Application Ser. No. 60/323,704, filed on Sep. 21, 2001, which is herein incorporated by reference.

FIELD OF THE INVENTION

The present invention relates to mutant-type lipases which demonstrate superior lipolytic and esterific activities. The mutant-type lipases are characterized by an amino acid alteration at the residue immediately followed either the serine residue or the histidine residue or both residues of the Ser-His-Asp catalytic triad. The amino acid residue that follows the serine residue of the Ser-His-Asp catalytic triad is alanine. The amino acid residue that follows the histidine residue of the Ser-His-Asp catalytic triad is isoleucine. The wild-type lipase is preferably from *Staphylococcus*, particularly *Staphylococcus epidermidis*. The present invention also relates to a method for preparing the mutant-type lipases by site-directed mutagenesis using PCR and a method for utilizing the mutant-type lipase to catalyze synthesis of flavor esters to be used in food industry.

BACKGROUND OF THE INVENTION

Lipases (triacyl glycerol hydrolase, EC 3.1.1.3) are widely distributed in nature. The principal biological function of lipase is the breakdown of lipids as an initial event in the utilization of fat as an energy source. The characteristic properties such as substrate specificity, regioselectivity and enantioselectivity among various lipases allow wide applications such as in the production of emulsifiers, fatty acid esters, fatty acids, and carbohydrate derivatives. (Liu & Shaw, *J. Am. Oil. Chem. Soc.* (1995), 72:1271-1274; Shaw & Wang, *Enzyme Microb. Technol.* (1991), 13:544-546; Wang et al., *Biotechnol. Bioeng.* (1992), 39:1128-1132 (1992)). A Ser-His-Asp catalytic triad occurs in lipases, which are responsible for hydrolyzing triglycerides into diglycerides and subsequently, monoglycerides and free fatty acids (Wallace et al., *Protein Science* (1996), 5:1001-1013).

The production of lipases is a general property of staphylococci, and lipase genes have been identified in *Staphylococcus aureus* strains PS54 and NCT8530, *Staphylococcus epidermidis* strain 9 and *Staphylococcus hyicus*. (Simons et al., *Eur. J. Biochem.* (1998), 253:675-683). The family of lipases from staphylococci demonstrates common structural features. For example, these enzymes are produced as preproenzymes, which have molecular masses of approximately 70 kDa. After secretion into the growth medium, proteolytic processing results in mature forms with molecular masses of 40-46 kDa. (Nikoleit et al., *Eur. J. Biochem.* (1995), 228:732-738).

*Staphylococcus epidermidis* strain 9 lipase gene (gehC) consists of a single open reading frame of 2064 nucleotides, which encoded a protein of 688 amino acids with a predicted molecular mass of 77 kDa. The gehC gene has been cloned and expressed in *Escherichia coli* by Simons et al (Eur. J. Biochem. 1998: 253(3): 675–683). In the extracts of *E. coli* harboring gehC, a lipase corresponding to the 77-kDa lipase but with an electrophoretic mobility equivalent to a 97-kDa protein has been detected. In the supernatant fluid of *S. epidermidis* strain 9 culture, a 43-kDa lipase of 386 amino acids has also been identified. It was suggested that the *S. epidermidis* lipase of 97 kDa electrophoretic mobility was secreted as a proprotein and subsequently cleaved between the Ala-302 and Lys-303 mino acid residues by a proteolytic enzyme to yield the 43-kDa lipase. However, no further structure-function studies on the Ser-His-Asp triad of the 43-kDa lipase have been carried out.

The lipase gene gehSE1 isolated from *S. epidermidis* strain RP62A was organized as a preproenzyme. A part of gehSE1 gene encoded the mature lipase of 380 amino acids that had a sequence similar to that of *S. epidermidis* strain 9 lipase from Asn-7 to Lys-386 with 97.8% homology. The gehSE1 mature lipase has been overexpressed as a fusion protein with an N-terminal His-tag in *E. coli* and characterized by Farrell et al., *J. Gen. Microbiol.* (1993), 139: 267-277.

Lipases have become increasingly important in biotechnology. The characteristic properties such as substrate specificity, regioselectivity and enantioselectivity among various lipases allow their wide applications, such as in the productions of emulsifiers, fatty acid esters, fatty acids and carbohydrate derivatives. In addition, there has been a strong demand in recent years for natural products, including natural flavors.

Esters are common flavor agents and are often employed in fruit-flavored products (e.g., beverages, candies, jellies, and jams), baked goods, wines, and dairy products (e.g., cultured butter, sour cream, yogurt, and cheese). Naturally occurring esters have been isolated from all major food systems and often are expensive.

Conventional production of flavor esters using chemical-catalyzed esterification requires high temperature and leads to dark-colored products and undesired byproducts. Enzyme-catalyzed conversion (biocatalysis) provides an alternative to the chemical syntheses of flavor esters. It is more efficient and selective. Inexpensive natural raw materials, such as fatty acids and alcohols, can be used in the enzyme-catalyzed synthesis of flavor esters (Manjon et al., *Biotechnol. Lett.* (1991), 13:339-344).

The use of lipolytic enzymes to catalyze the esterification reaction for producing flavor esters has been investigated by many workers. However, current methods using lipolytic enzymes were performed in hydrophobic organic solvents or in aqueous-organic two-phase systems. The uses of organic solvents carry the risks of flammability as well as toxicity to the production workers and the environment. Residual organic solvents may cause a safety concern for the consumers. Thus, the needs for a safe and more effective biocatalytic system remain unfulfilled.

SUMMARY OF THE INVENTION

The present invention provides isolated and purified mutant-type lipases which contain a serine-histidine-aspartic acid catalytic triad. The lipases are further characterized by having an amino acid alteration in the residue immediately following either the serine residue, or the histidine residue, or both the serine and the histidine residues of the serine-histidine-aspartate ("Ser-His-Asp") catalytic triad. In the mutant-type lipase, the amino acid residue that follows the serine residue of the Ser-His-Asp catalytic triad is alanine, the amino acid residue that follows the histidine residue is isoleucine. Preferably, the last amino acid residue of the lipase is replaced with a glutamic acid residue, and six histidine residues are further added to the C-terminus of this glutamic acid residue.

The mutant-type lipase is preferably obtained from site-directed mutagenesis of a lipase isolated from *Staphylococcus*, most favorably *Staphylococcus epidermidis*. The mutant lipase from *Staphylococcus epidermidis* that has an alanine residue replacing the methionine residue which immediately follows the serine residue of the Ser-His-Asp catalytic triad has the amino acid sequence of SEQ ID NO: 15. The mutant lipase from *Stapylococcus epidermidis* that has an isoleucine residue replacing the valine residue which immediately follows the histidine residue of the Ser-His-Asp catalytic triad has the amino acid sequence of SEQ ID NO: 17.

The mutant-type lipases of the present invention have both lipolytic and esterific activity to either hydrolyzes the fatty acid ester or esterify fatty acids with alcohols. The mutant-type lipases' esterification reaction does not require the use of organic solvents such as n-hexane. In fact, the mutant-type lipases from *Staphylococcus epidermidis* become inactive in n-hexane.

The present invention also provides a method for producing the mutant-type lipase which comprises: (1) synthesizing a mutant gene encoding the mutant-type lipase by a site-directed mutagenesis using polymerase chain reaction (PCR); (2) ligating the mutant gene to a plasmid; and (3) transfecting the ligated plasmid into a host cell to overexpress the lipase.

The site-directed mutagenesis method used in the present invention is according to Sharrocks and Shaw, *Nucleic Acids Res*. (1992), 20:1147, which is herein incorporated by reference. To make a mutant agene, a three-primer PCR method is employed, which requires the use of a single mutagenic primer in conjunction with two flanking, universal primers. For example, to make a mutant gene with an alanine residue following the serine residue in the Ser-His-Asp catalytic triad of the mutant-type lipase, an N-terminal oligonucleotide primer such as SEQ ID NO:1, a C-terminal oligonucleotide primer such as SEQ ID NO:2 and a mutagenic primer such as SEQ ID NO:6 can be used. Alternatively, to make a mutant gene with an isoleucine residue following the histidine residue in the Ser-His-Asp catalytic triad of the mutant-type lipase, an N-terminal oligonucleotide primer such as SEQ ID NO:1, a C-terminal oligonucleotide primer such as SEQ ID NO:2 and a mutagenic primer such as SEQ ID NO:11 can be used.

The mutant gene is further digested with restriction endonucleases, such as NcoI and XhoI, followed by ligation to a plasmid, such as pET-20b(+). The mutant gene-ligated plasmid is then transfecting a host cell, preferably a prokaryotic cell, such as *Escherichia coli*.

To create a restriction enzyme cleavage site necessary for cloning, the last codon at the 3' end is changed to a glutamic acid codon. Also, to facilitate purification of the mutant-type lipase, 6 histidine residues are added to the 3'-end of the glutamic acid codon. The mutant-type lipase with 6 histidine residues at the C-terminus is purified by an $NiSO_4^-$ charged His-bind resin column.

Furthermore, the present invention provides a method for enhancing flavor in food which comprises enzymatically synthesizing a flavor ester from alcohol and fatty acid by the mutant-type lipase and adding the flavor ester to the food. For the mutant-type lipase which has an alanine immediately following the serine residue of the Ser-His-Asp catalytic triad, the preferred alcohol is a primary alcohol with carbon-chain length from 2 to 16. The most favorable flavor ester is decyl myristate or decyl oleate. For the mutant-type lipase which has an isoleucine residue immediately following the histidine residue of the Ser-His-Asp catalytic triad, the preferred alcohol is a primary alcohol with carbon-chain length from 2 to 12. The preferred flavor ester is decyl laurate. The flavor ester can be added to fruit-flavored products (such as beverages, candies, jellies, and jams), baked goods, wines, and dairy products (such as cultured butter, sour cream, yogurt, and cheese).

BRIEF DESCRIPTION OF DRAWINGS

FIG. 1 shows the expression of the recombinant *S. epidermidis* lipase with 6 X His-tail in *E. coli* BL21 (DE3). Cells were harvested 4 hours after IPTG induction and sonicated. Proteins of the respective cellular extracts were separated by SDS/PAGE. Part A and Part B show the Coomassie Brilliant Blue stains and the esterase activity stains, respectively, of protein molecular weight markers (lane 1); proteins from BL21(DE3) containing pET-20b(+) (lane 2); proteins from BL21(DE3) containing pET-20b(+) with *S. epidermidis* lipase gene (lane 3); and lipase purified with His-Bind resin (lane 4).

DETAILED DESCRIPTION OF THE INVENTION

The Ser-His-Asp catalytic triad can be found in serine proteases and lipases, which is one of the best known and most intensively studied of all functional mechanisms. In the Ser-His-Asp catalytic triad, the three residues, which occur far apart in the amino acid sequence of the enzyme, come together in a specific conformation in the active site to perform the hydrolytic cleavage of the appropriate bond in the substrate. This triad was first identified in the serine proteinases, which cleave peptides at the amide bond. Apart from the serine proteases, the Ser-His-Asp catalytic triad also occurs in the triacylglycerol lipases, which are responsible for hydrolyzing triglycerides into diglycerides and, subsequently, monoglycerides and free fatty acids. A comprehensive study of the Ser-His-Asp catalytic triad is disclosed by Wallace et al., *Protein Science* (1996), 5:1001–1013, which is herein incorporated by reference.

The present invention focuses on modification(s) of the catalytic site of lipases, particularly surrounding the Ser-His-Asp catalytic triad. The modification(s) are directed to site mutation of the codon following the serine residue, the histidine residue, or both residues of the Ser-His-Asp catalytic triad, using site-directed mutagenesis.

Site-directed mutagenesis is an important procedure in studies of gene expression and protein structure/function relationships. A variety of protocols have been developed to mutate specific bases in plasmid DNA, which employ oligonucleotide primers containing desired mutations flanked by bases complementary to target sequences.

Sharrocks and Shaw, *Nucleic Acid Res*. (1992), 20:1147, discloses an improved primer design for PCR-based, site-directed mutagenesis. The method requires a single mutagenic primer, which is used in conjunction with two flanking, universal primers in a dual step of PCR amplication. The method further involves the design of the mutagenic primer such that its 5' end immediately follows the wobble position of a codon. The wobble position is referred to as the third base of the codon, which is less stringent for codon recognition than the other two bases. This design tolerates the addition of any nucleotide (or none) at the 3' end of the complementary strand without ensuing consequences and has the further advantage that wobble positions occur, with few exceptions, at every third nucleotide.

Based on the method suggested by Sharrocks and Shaw, supra, a number of mutagenic primers can be designed in accordance with the specific lipase gene sequences, which then can be utilized for production of the mutant-type lipases. Specifically, the mutagenic primers can be used for preparing a mutated codon following either the serine residue or the histidine residue of the Ser-His-Asp catalytic triad. These mutagenic primers applied to mutations of any lipases containing a Ser-His-Asp catalytic triad, such as lipases isolated from gram positive or gram negative bacteria, or fungi. Examples of gram positive bacteria which contain lipases include, but are not limited to S. epidermidis, S. hyicus, S. aureus, B. thermocatenularus, S. xylosus, and S. warneri. Examples of gram negative bacteria which contain lipases include, but are not limited to, A. calcoaceticus, Arthrobacter sp., P. aeruginosa, P. cepacia, P. vulgaris, and S. marcescens. Examples of fungi include, but are not limited to, H. lanuginosa, Candida cylindracea, and R. oryzae.

The following examples are illustrative, but not limiting the scope of the present invention. Reasonable variations, such as those occur to reasonable artisan, can be made herein without departing from the scope of the present invention. Also, in describing the invention, specific terminology is employed for the sake of clarity. However, the invention is not intended to be limited to the specific terminology so selected. It is to be understood that each specific element includes all technical equivalents which operate in a similar manner to accomplish a similar purpose.

In the examples to be presented below, the enzymes used in the recombinant DNA experiments were purchased from either Promega Co. (Madison, Wis.) or B. M. Biochemicals (Mannheim, Germany). Oligonucleotide primers were made by Bio-Synthesis Co. (Taipei, Taiwan). Taq DNA polymerase and DNA sequencing kit were obtained from HT Biotechnology Ltd. (Cambridge, England) and U.S. Biochemicals (Cleveland, Ohio), respectively. *Escherichia coli* HB101 (Boyer and Roulland-Dussoix 1969) was provided by Promega Co. *Escherichia coli* BL21(DE3) and plasmid pET-20b(+) were obtained from Novagene Co. (Madison, Wis.). A geneclean kit was purchased from Bio101 Co. (Vista, Calif.) and a plasmid DNA purification kit was purchased from Promega Co. Isopropyl thio-β-D-galactoside (IPTG) was obtained from B. M. Biochemicals. Oleic acid butyl ester, oleic acid lauryl ester, eicosapentaenoic acid (EPA), docosahexaenoic acid (DHA), fatty acids, and alcohols were purchased from Sigma Co. Silica gel 60, hexane, 2-propanol, and acetone were purchased from Merck Chemical Co. Protein molecular weight markers were obtained from Novel Experimental Technology Co. Other chemicals were reagent grades. Double-distilled water was used throughout the experiment.

The bacteria were grown at 37° C. or 30° C. in L-broth (LB) or on LB/1.5% bacto-agar plates. Ampicillin (50 mg/ml final) was added when needed.

EXAMPLE 1

Cloning of Lys-303 Gene From *S. epidermidis* Strain 9

A fragment of the gehC gene (designated "Lys-303" gene), which encoded an amino acid sequence corresponding to that of the *S. epidermidis* lipase following proteolytic cleavage between Ala-302 and Lys-303, was synthesized by polymerase chain reaction (PCR) using a chromosomal DNA from a *S. epidermidis* isolated from a patient in Chang-Gung Hospital (Keelung, Taiwan) as template. The gehC gene is a *Staphylococcus epidermidis* strain 9 lipase gene. The gene consisted of a single open reading frame of 2064 nucleotides, which encoded a protein of 688 amino acids with a predicted molecular mass of 77 kDa. The Lys-303 gene (SEQ ID NO:13) encoded an active lipase (SEQ ID NO:14), which was about 43 kDa in molecular weight. The Lys-303-encoded lipase is also known as the "43 kDa" or "wild-type" lipase. Two primers: an N-terminal primer of SEQ ID NO:1 (5'-GGGGCCATGGAACAAAAA-CAATATAAAAAT-3') and a C-terminal primer of SEQ ID NO:2 (5'-GGGGCTCGAGTTTATTTGTTGATGT-TAATTG-3') were used in this synthetic process.

The product of the PCR was digested with NcoI and XhoI, ligated to a 3.7 kb NcoI/XhoI-digested pET-20b(+) DNA fragment. The ligated pET-20b(+) was then transformed into *E. coli* HB101 (Promega) and into *E. coli* BL21 (DE3) (Novagen). The DNA sequence of the Lys-303 gene was confirmed with plasmid isolated from BL21 (DE3) and was identical to *S. epidermidis* strain 9 lipase gene. All recombinant DNA experiments followed standard protocols or protocols recommended by manufacturers. The expressed lipase contained six additional histidine residues attached at the C-terminus. The 6 histidine residues were added to facilitate the enzyme purification using a $NiSO_4^-$ charged His-bind resins (Novagene Colo.).

EXAMPLE 2

Site-directed Mutagenesis

Mutant genes were synthesized from *S. epidermidis* chromosomal DNA by a two-step, three-primer PCR method in which the N-terminal and C-terminal oligonucleotides were identical to those used for the synthesis of the "Lys-303" gene (i.e., SEQ ID NO:1 and SEQ ID NO:2), as described in Example 1. The oligonucleotide primers for the mutation sites are listed in Table 1. The products of the PCR were digested with NcoI and XhoI, and were ligated to a NcoI/XhoI-predigested pET-20b(+) DNA fragment. The desired ligated products were cloned, first into *E. coli* HB101, then into *E. coli* BL21 (DE3). The DNA sequences surrounding mutant codons were determined (Sanger et al. 1977) from the plasmids isolated from *E. coli* BL21 (DE3).

TABLE 1

Oligonucleotides Used for the PCR-Site-Directed Mutagenesis of the *S. epidermidis* "Lys-303" Recombinant Lipase Genea[a]

| Primers | Sequence No. | Oligonucleotides |
|---|---|---|
| wild-type | SEQ ID NO:3 | 5'-GACCACCCATACTATGACCAAC-3' |
| S418C | SEQ ID NO:4 | 5'-ACCCATACAATGACCAAC-3' |
| M419L | SEQ ID NO:5 | 5'-GACCACCGAGACTATGACCAAC-3' |
| M419A | SEQ ID NO:6 | 5'-GACCACCGGCACTATGACCAAC-3' |
| M419Q | SEQ ID NO:7 | 5'-GACCACCTTGACTATGACCAAC-3' |
| wild-type | SEQ ID NO:8 | 5'-GGGATCATGTAGACTTTGTAGG-3' |
| H648K | SEQ ID NO:9 | 5'-TGGGATAAAGTAGACTTT-3' |
| V649L | SEQ ID NO:10 | 5'-GGGATCATCTCGACTTTGTAGG-3' |
| V649I | SEQ ID NO:11 | 5'-GGGATCATATCGACTTTGTAGG-3' |
| V649A | SEQ ID NO:12 | 5'GGGATCATGCTGACTTTGTAGG-3' |

[a]Capital letters denote wild-type and mutant type nucleotide, respectively. The mutated nucleotide is shown in bold.
PCR, polymerase chain reaction.

EXAMPLE 3

Expression of the Wild-type or Mutant-type Lipases

E. coli BL21 (DE3) cells harboring the desired wild-type lipase gene (i.e., the Lys-303 gene) on plasmid pET-20b(+), were grown at 30° C. in LB/ampicillin to an optical density (600 nm) of 0.5. IPTG was added to the cultures (100 mL each) for a final concentration of 4 mM, and the cells were harvested four hours after the IPTG induction. IPTG is β-D(−)-thiogalactopyranoside, which induces the expression of a recombinant gene.

EXAMPLE 4

Purification and Quantification of the Wild-type or Mutant-type Lipases

For protein purification of the wild-type or mutant-type lipase, the cells, which were suspended in a buffer of 20 mM Tris/HCl (pH 7.9), 5 mM imidazole, 0.5 M NaCl, and 0.05% Tween 20, were broken on ice (10×30 s at 50 W) in a Microson Ultrasonic Cell Disruptor (Microsonix Inc., New York, N.Y.) and then centrifuged at 10,000×g. The proteins in the supernatant fraction were separated by sodium dodecyl sulfate/polyacrylamide gel electrophoresis (SDS/PAGE). The separated proteins were stained with Coomassie Brilliant Blue and assayed for the esterase activity on gels after the removal of SDS.

Supernatant fractions with positive gel esterase results were loaded into $NiSO_4^-$ charged His-bind resins (Novagene Colo.). After binding, the resins were washed with a buffer containing 20 mM Tris/HCl (pH 7.9), 60 mM imidazole, and 0.5 M NaCl. The lipase was eluted with another buffer, containing 20 mM Tris/HCl (pH 7.9), 1 M imidazole, and 0.5 M NaCl, and dialyzed against a 50 mM phosphate buffer (pH 6.8). Protein concentrations were determined according to a dye-binding procedure (Bradford 1976), using the Bio-Rad protein assay kit system.

EXAMPLE 5

Preparation of Immobilized Lipases

To study the effect of n-hexane content on the lipase-catalyzed synthesis, the E. coli cells harboring the wild-type or mutant-type lipase gene were broken on ice by an ultrasonic cell disrupter. After centrifugation, the supernatant fraction containing the crude enzyme was dialyzed against a 50 mM phosphate buffer (pH 6.0). Crude enzyme solution (1 mL) was mixed with 1 g of silica gel 60 and left for 30 min at 4° C. The gel was precipitated by 8 mL acetone (prechilled at 4° C.) and dried in a vacuum-dryer. The immobilized wild-type or mutant-type lipase was transferred to a flask and further vacuum dried at ambient temperature.

EXAMPLE 6

Esterification Reaction and Ester Analyses

The lipase solutions in 50 mM phosphate buffer (pH 6.0) were added to a reaction mixture (1 mL) containing 50 mM fatty acids and 50 mM alcohols. The reaction was carried out in screw capped bottles (with 22-mm diameter) and the reaction mixture was incubated at 33° C. in an orbital shaker with a speed of 250 rpm.

At various time intervals, products were extracted in 1 mL of hexane, and 1.5 µL of the reaction mixture was withdrawn and analyzed by gas chromatography (Hitachi model 263-30; Hitachi, Tokyo, Japan). A DB-1 fused-silica capillary column of 15 m×0.32 mm i.d. (J & W Corporation, Calif.) was used. Nitrogen gas was the carrier gas at a flow rate of 1.2 mL/min. The injection port and flame ionization detector temperatures were programmed to start at 120° C., then raise at 20° C./min to 250° C., and hold at 250° C. for 7 min. The product compositions were quantitated by an integrator with oleic acid lauryl ester or oleic acid butyl ester as the internal standard. The conversion yield was calculated on the basis of the limited substrate.

EXAMPLE 7

Enzyme Assay

The purified enzymes and substrate p-nitrophenyl butyrate (2.64 mM predissolved in 2.1% Triton X-100) were mixed in 50 mM phosphate buffer (pH 6.0). The reactions were carried out at 37° C. for 15 min and were terminated by the addition of acetone (1:1, v/v) (Kazlauskas 1994). The absorption values of the reaction product (p-nitrophenol) at 346 nm were determined, and the hydrolase activity (a general indicator for the lipolytic activity) of the purified enzymes was obtained, after converting the absorption values into mmols of p-nitrophenol quantity (at pH 6.0) curve. The molar extinction coefficient of p-nitrophenol under this condition was 2988° C./M·cm.

Results and Discussions

1. Cloning of the Wild-Type and Mutant-Type Lipase from S. epidermidis Strain 9

The nucleotide sequence of the gehC Lys-303 gene fragment cloned from a strain of S. epidermidis, isolated from a patient in Chang-Gung Hospital (Keelung, Taiwan) was identical to the S. epidermidis 9 lipase gene reported previously by Simons et al. Eur. J. Biochem. (1998), 253: 675–683, supra. To form a restriction enzyme cleavage site necessary for the cloning, the Lys-303 was changed to Glu. Six histidine residues were added to the C-terminal of the lipase to facilitate enzyme purification.

Figure 1:
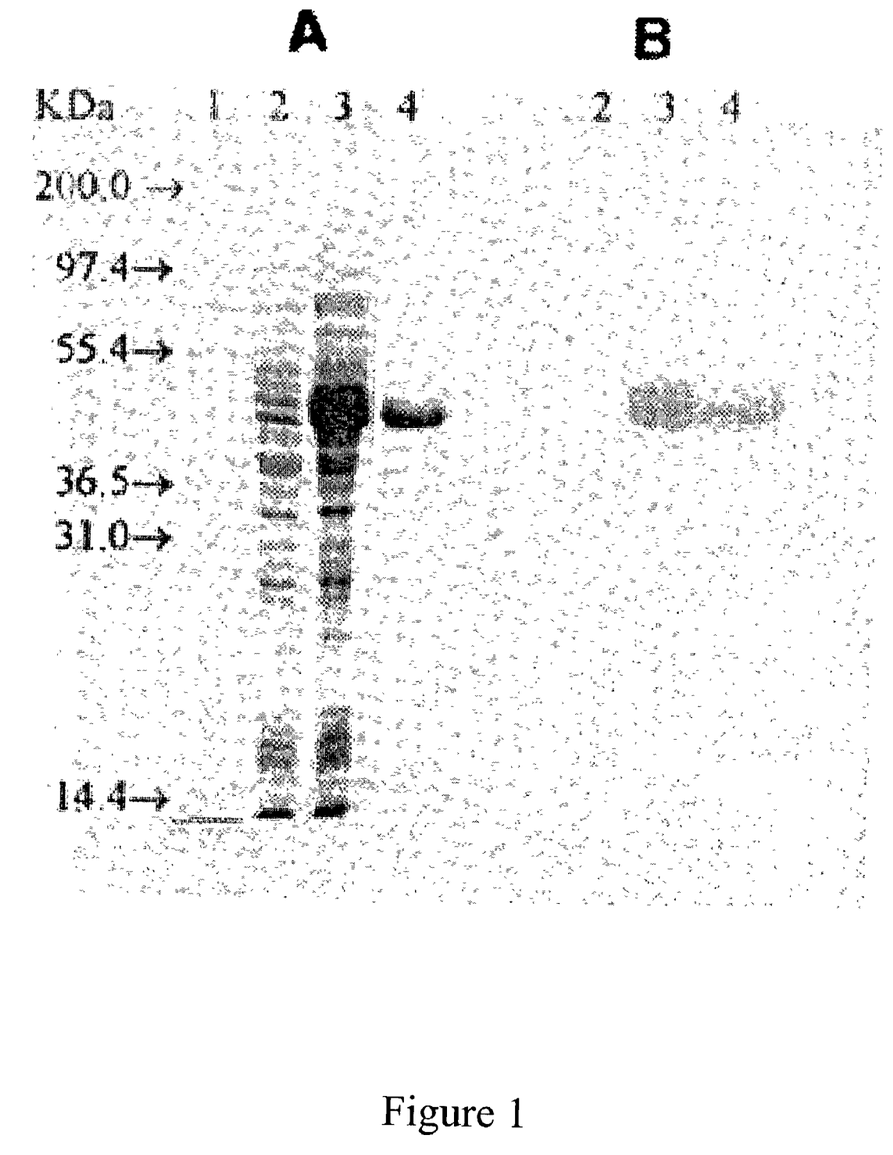

As shown in FIG. 1, this slight modification did not retard the overexpression of the lipase gene in E. coli BL21 (DE3) or destroy the enzyme activity. The purified protein showed a single major band at 43 kDa on SDS/PAGE and on general esterase activity stains (FIG. 1). This finding agreed with the previous report of Farrel et al., J. Gen. Microbiol. (1993), 139:267–277, supra, that S. epidermidis produced a lipase at 97 kDa on SDS/PAGE, which was proteolyticly degraded by S. epidermidis to a 43-kDa form.

The amino acid sequence of the wild-type lipase was nearly identical (97.8% identity) to the lipase gene of S. epidermidis strain 9 (RP62A) reported by Simons et al. except that tyrosine-453 was replaced by phenylalanine, and glutamic acid-675 was replaced by aspartic acid.

The results of the this study demonstrated that a 43-kDa S. epidermidis strain 9 full length mature lipase could be overexpressed in E. coli and purified easily with a C-terminal His-tag by immobilized Ni-resin column.

2. pH Profile of the Recombinant Lys-303 Lipase

The pH-activity profile for the wild-type "Lys-303" lipase was investigated using p-nitrophenyl butyrate as a substrate. As shown in Table 2, the optimal pH for enzyme activity was found to be 6.0. This result was similar to the recombinant lipases of S. epidermidis strain RP62A disclosed by Simmon et al.

TABLE 2

Effect of pH on the Recombinant *S. epidermidis* Lipase[a]

| pH | Relative activity (%) |
| --- | --- |
| 3.0 | 0 |
| 4.0 | 4 |
| 5.0 | 23 |
| 6.0 | 100 |
| 7.0 | 76 |
| 8.0 | 35 |

[a]The activity was assayed at 37° C. using p-nitrophenyl butyrate as substrate (2.64 mM) in 50 mM Good's buffer (mixture of BICINE [N, N-bis (2-hydroxyethyl)-glycine], CAPS [3-(cyclohexylamino)-1-propane sulfonic acid], sodium acetate and bis-Tris propane, 50 mM each, adjusted to desired pH by HCl or NaOH). The relative activity at a given pH was calculated by dividing the absolute reaction rate by that at pH 6.0.

Temperature Profile of the Recombinant Lys-303 Lipase

Enzyme activities at various temperatures were analyzed with p-nitrophenyl butyrate as substrate. As shown in Table 3, the lower temperatures were found to be favored, with an optimum at 25° C.

TABLE 3

Effect of Temperature on the Activity of Recombinant *S. epidermidis* Lipase[a]

| Temperature (° C.) | Relative activity (%) |
| --- | --- |
| 5 | 31 |
| 10 | 47 |
| 15 | 66 |
| 20 | 87 |
| 25 | 100 |
| 30 | 98 |
| 35 | 77 |
| 40 | 23 |
| 45 | 3 |
| 50 | 2 |

[a]Lipase activity was monitored by the formation of p-nitrophehol from p-nitrophenyl butyrate. The relative activity at a given temperature was calculated by dividing the absolute rate by that at 25° C.

3. Site-directed Mutagensis and Substrate Specificity

For the convenience of this study, the positions of the serine, histidine, and aspartic acid residues of the Ser-His-Asp catalytic triad of the wild-type and/or mutant-type lipase from *S. epidermidis* were numbered after the amino acid sequence of the preproenzyme. The *S. epidermidis* strain 9 preproenzeme has a molecular weight of approximately 77 kDa, which contains 688 amino acids.

Under this numbering system, the serine residue was at position 418 ("Ser-418"), the aspartic acid residue was at position 609 ("Asp-609"), and the histidine residue was at position 648 ("His-648"). The triad positions of Ser-418, Asp-609, and His-648 were consistent in both *S. epidermidis*, *S. aureus*, and *S. hyius*.

Site-directed mutagenesis experiments were performed to study the role of the amino acid residues at the catalytic triad (i e, the serine, histidine, or aspartic acid residues) and the amino acid residues following the serine residue and the histidine residue were Met-419 and Val-649 of the Ser-His-Asp catalytic triad.

For mutant S418C (where the serine residue at the catalytic triad was replaced by a cysteine residue), no general lipolytic activity was detected on gels following electrophoresis although a predominant overexpressed 43-kDa protein was detected by Coomassie Brilliant Blue staining. Furthermore, no significant levels of esterase activity were detected from S418C extracts, when compared to those of wild-type extracts. The results strongly suggested that Ser-418 was a member of catalytic triad since simply changing the hydroxyl group to a thiol group caused the loss of enzyme activity.

For mutant H648K (i.e., the histidine residue of the catalytic triad was replaced by lysine), having the amino acid sequence of SEQ ID NO:16, the protein expressed in *E. coli* exhibited very low lipolytic activity on gels when compared to that of wild-type cells. When compared with the wild-type enzyme, mutant H648K showed little change in the $K_m$ for substrate p-nitrophenyl butyrate, but the $k_{cat}$ greatly decreased to 10.4% (Table 4). The results suggested that H648 was critical for catalysis but not for substrate binding.

TABLE 4

Kinetic Parameters for Wild-type and Mutants of *S. epidermidis* Lipase[a]

| Enzyme | $K_m$(mM) | $k_{cat}(s^{-1})$ | $K_{cat}/K_m(s^{-1} \cdot mM^{-1})$ |
| --- | --- | --- | --- |
| Wild-type | 0.90 ± 0.08 | 25.1 ± 0.6 | 27.9 |
| M419A | 3.97 ± 0.12 | 217.6 ± 14.0 | 54.8 |
| H648K | 0.95 ± 0.35 | 2.6 ± 0.9 | 2.7 |
| V649I | 3.02 ± 0.21 | 335.8 ± 15.7 | 111.2 |

[a]Lipase activity was monitored by the formation of p-nitrophenol from p-nitrophenyl butyrate. Data were obtained from three experiments and expressed as means ± standard error.

The amide NH group of the catalytic serine has been suggested to involve in the stabilization of the oxyanion that forms the tetrahedral intermediate in the reaction through hydrogen bond formation. To study the role of the residue following the catalytic serine, site-directed mutants were constructed using the mutagenic primers listed in Table 1, supra.

For mutant enzymes M419L (i.e., the methionine at position 419 was replaced by a leucine) and M419Q (i.e., the methionine at position 419 position was replaced by glutamine), no general lipolytic activity was detected on gels.

For M419A (i.e., the methionine at position 419 was replaced by an alanine), the mutant-type enzyme showed increased lipolytic activity on gels as compared with the wild-type enzyme. The mutation apparently affected the enzyme's ability to stabilize the transition state more than it affected the substrate binding ability of the enzyme. Kinetic analysis using p-nitrophenyl butyrate as substrate (Table 4) showed that in comparison with the wild-type enzyme, the M419A increased the catalytic efficiency ($k_{cat}/K_m$) by 2.0 fold, which was dominated by $k_{cat}$ effect. $K_m$ is the Michaelis-Menten constant, which shows the concentration of substrate (e.g., mM) at which half the active sites are filled. $k_{cat}$ (e.g., $s^{-1}$) is the maximal catalytic rate when substrate is saturating. The $k_{cat}/K_m$ ratio is the pertinent parameter to determine kinetic efficiency of an enzyme.

The kinetic results in Table 4 demonstrated that the amino acid residue following the catalytic serine not only was involved in the stabilization of oxyanion hole (as seen by alteration of $k_{cat}$) but also was an important determinant for substrate binding and specificity (as indicated by the alteration of $K_m$ in the mutants), presumably defined by the amino acid's side chain.

The mutation of Met-419 to Ala significantly broadened the specificity of the enzyme and increased the activity toward larger substrates. As shown in Table 5, the best substrates for wild-type and M419A enzymes were p-nitrophenyl butyrate and p-nitrophyl carprate, respectively. Among the p-nitrophenyl esters tested, the M419A mutant enzyme showed increased activity than the wild-type enzyme toward all substrates except p-nitrophenyl stearate.

TABLE 5

Substrate Specificity of the Recombinant *S. epidermidis* Lipase and Mutant Type Lipases[a]

| Substrate | Relative activity (%) | | |
|---|---|---|---|
| | wild-type | M419A | V649I |
| p-nitrophenyl acetate | 19.31 | 140.89 | 321.84 |
| p-nitrophenyl butyrate | 100.00 | 189.99 | 550.22 |
| p-nitrophenyl caproate | 37.45 | 145.04 | 199.49 |
| p-nitrophenyl caprylate | 43.02 | 154.65 | 264.48 |
| p-nitrophenyl caprate | 74.33 | 227.29 | 338.32 |
| p-nitrophenyl laurate | 37.78 | 128.46 | 113.50 |
| p-nitrophenyl myristate | 12.59 | 40.19 | 18.65 |
| p-nitrophenyl palmitate | 5.46 | 11.19 | 2.43 |
| p-nitrophenyl stearate | 8.14 | 0.78 | 0.00 |

[a]Lipase activity was monitored by the formation of p-nitrophenol from p-nitrophenyl ester. Relative activities were calculated by dividing the absolute activities by that of the p-nitrophenyl butyrate for wild-type (9440 μmol/μg/min). Each data point was the average value of three independent measurements.

The amino acid residues following His-648 could presumably affect the substrate specificity and/or catalytic efficiency. To study the role of Val-649, site-directed mutants were constructed. Mutants V649A (i.e., the valine residue at position 649 was replaced by an alanine residue) and V649L (i.e., the valine residue at position 649 was replaced by a leucine residue) lost enzyme activity.

On the contrary, a V649I mutant enzyme showed improvement in the specific activity for the hydrolysis of p-nitrophenyl butyrate over that of wild-type enzyme (Table 5). In comparison with the wild-type enzyme, the V649I enzyme showed a 4.0-fold increase in the $k_{cat}/K_m$ and a 13.4 fold increase in $k_{cat}$ toward substrate p-nitrophenyl butyrate (Table 4). These suggested that Val-649 affected enzyme catalysis.

The above facts suggested that the amino acid residues following catalytic Ser-418 significantly influenced the substrate preference and/or catalytic efficiency of the enzyme. In comparison with the wild-type enzyme, the M419A mutant enzyme preferred p-nitrophenyl carprate (Table 5). The substitution with a smaller side chain in M419A might enlarge the pocket of the catalytic site, enabling the binding and hydrolysis of substrates with longer carbon chain. The active site became more plastic. Furthermore, V649I was better suited for p-nitrophenyl caprate, and this phenomenon was likely to be a slight increase in the hydrophobicity around the substrate binding site, which might influence certain kinetic behaviors of the lipase. Therefore, Val-649 could play an important role in the substrate specificity and could serve as a good candidate for the engineering of enzyme specificity.

As shown in Table 5, among the esters of p-nitrophenol tested, the preferred substrate for the wild-type *S. epidermidis* strain 9 lipase was the butyrate ester. This finding was similar to that of *S. epidermidis* strain RP62A lipase reported by Simons et al.

As shown in Table 5, the substrate specificity of the wild-type and mutant-type lipases in the present invention were similar to those reported by Simon et al., supra, in *S. epidermidis* strain RP62A lipases. Also, as shown in Table 4, kinetic analyses using p-nitrophenyl butyrate as substrate showed $K_m$, $k_{cat}$ and $k_{cat}/K_m$ of the wild-type *S. epidermidis* strain 9 lipase were 0.90 mM, 25.1 s$^{-1}$ and 28.2 s$^{-1}$ mM, respectively. In comparison, the $K_m$, $k_{cat}$ and $k_{cat}/K_m$ of *S. hyicus* lipase were reported 2.07 mM, 0.53 s$^{-1}$ and 0.257 s$^{-1}$ mM$^{-1}$, respectively. (Chang et al., Biochem. Biophys. Res. Commun. (1996), 229:6–10). The *S. epidermidis* lipase had much higher substrate-binding affinity and catalytic efficiency than the *S. hyicus* lipase.

4. Effect of n-Hexane Content on the Ester Synthesis

It was reported that the use of lipolytic enzymes to catalyze the esterification reaction for producing flavor esters required organic solvent and the formation of ester might be influenced by the water content in organic solvent. In the present study, the immobilized wild-type *S. epidermidis* was used for the enzymatic synthesis of octyl oleate in n-hexane with different water content. The results are shown in Table 6. Surprisingly, the yields of esterification were inversely proportional to the n-hexane content of the system (Gatfield 1986). In the most successful attempts, it was found that organic solvents nearly always exerted deleterious effects on catalysis by both free and immobilized enzymes. This result revealed that *S. epidermidis* lipase became inactive in the n-hexane system, and an aqueous buffer system would be essential for the catalytic activity of the *S. epidermidis* lipase.

TABLE 6

Effect of n-hexane Content on the Synthesis of Octyl Oleate by the Wild-Type *S. epidermidis* Lipase[a]

| n-hexane content (%) | yield (%)[b] |
|---|---|
| 0 | 46.5 |
| 10 | 26.5 |
| 20 | 11.0 |
| 30 | 4.3 |
| 40 | 3.5 |
| 50 | 3.0 |
| 60 | 2.7 |
| 70 | 1.9 |
| 80 | 1.2 |
| 90 | 0 |
| 100 | 0 |

[a]Lipase was immobilized on silica gel 60 as described in Example 5. Immobilized wild-type lipase (0.15 g, 21,500 units), 50 mM oleic acid, and 50 mM octanol in 1 mL mixture solvent of hexane and 50 mM phosphate buffer (pH 6.0) was shaken at 250 rpm for 10 hours at 33° C. Enzyme unit was measured by the hydrolysis of p-nitrophenyl butyrate as substrate. One unit of enzyme was defined as the amount of enzyme that produced 1 μmol of p-nitrophenol/min.
[b]The percentage of yield was defined as the molar ratio of the resultant ester to the original reactant.

5. Esterification Reaction

To study the effect of esterification time, the yield of lauryl oleate as a function of esterification time are shown in Table 7. The yield of lauryl oleate catalyzed by the wild-type and mutant *S. epidermidis* lipase reached a maximum at 12 hours and then slightly decreased. For convenience and to standardized experiments, the esterification reaction was carried out for 10 hours for convenience.

TABLE 7

Effect of Reaction Time on Synthesis of Lauryl Oleate by the Wild-Type *S. epidermidis* Lipase[a]

| reaction time (h) | yield (%)[b] |
|---|---|
| 3 | 11.1 |
| 6 | 47.7 |

TABLE 7-continued

Effect of Reaction Time on Synthesis of
Lauryl Oleate by the Wild-Type S. epidermidis Lipase[a]

| reaction time (h) | yield (%)[b] |
|---|---|
| 9 | 63.1 |
| 12 | 68.8 |
| 15 | 67.3 |
| 18 | 64.4 |
| 22 | 65.8 |
| 24 | 63.1 |
| 48 | 64.2 |
| 128 | 53.1 |

[a]The wild-type enzyme (19,200 units) was added to a reaction mixture (1 mL) containing 50 mM oleic acid and 50 mM lauryl alcohol in 50 mM phosphate buffer (pH 6.0) and reacted at 33° C. The reaction times were 3, 6, 9, 12, 15, 18, 22, 24, 48, and 128 hours.
[b]The percentage of yield was defined as the molar ratio of the resultant ester to the original reactant.

6. Effects of Chain Length of Acyl Donors on Synthesis of Decyl Esters Catalyzed by Wild-type or Mutant-type Lipase The yields of esters synthesis catalyzed by wild-type or mutant-type lipase were affected by the carbon chain length of the acyl donors. The experiment, as shown in Table 8, was designed to study the yield of decyl esters when lauryl alcohol was reacted with a primary acid with various carbon chain length.

TABLE 8

Effect of Chain Length of Primary Acids on the Synthesis of
Decyl Esters by the Recombinant S. epidermidis Lipases[a]

| | yield (%)[b] | | |
|---|---|---|---|
| primary acid | wild type | M419A | V649I |
| acetic acid | 0 | 0 | 0 |
| butyric acid | 0 | 0 | 0 |
| hexanoic acid | 0.85 | 0 | 1.55 |
| octanoic acid | 23.1 | 11.97 | 23.1 |
| decanoic acid | 24.79 | 0.50 | 25.85 |
| lauric acid | 59.58 | 16.76 | 51.41 |
| myristic acid | 31.69 | 40.85 | 17.04 |
| palmitic acid | 13.94 | 12.82 | 13.17 |
| stearic acid | 12.11 | 11.69 | 12.11 |
| arachidonic acid | 2.11 | 12.68 | 0 |

[a]The enzyme (16,500 units) was added to a reaction mixture (1 mL) containing 50 mM oleic acid and 50 mM lauryl alcohol in 50 mM phosphate buffer (pH 6.0) and reacted at 33° C. for 10 hours.
[b]The percentage of yield was defined as the molar ratio of the resultant ester to original reactant.

As shown in Table 8, both the wild-type and the V649I mutant-type lipase showed higher yields of ester when medium-chain fatty acids (from $C_8$ to $C_{14}$) were used. The optimal yield came from lauric acid, which contains a carbon chain length of $C_{12}$, for both the wild-type and the V649I mutant-type lipase.

The M419A mutant-type lipase demonstrated slight improvement on the yields of esters over the wild-type lipase when longer carbon chains of the primary acids were used as the acyl donors. The optimum fatty acid for M419 mutant-type lipase was mysristic acid, which contains a carbon chain length of $C_{14}$.

The above finding suggested that that Met-419, the amino acid residue which follows the serine residue of the Ser-His-Asp catalytic triad, might play a dominant role in the acid-binding. On the contrary, Val-649, the amino acid residue which follows the histidine residue of the Ser-His-Asp catalytic triad, might not affect the acid-binding. This was based on the findings, as shown in Table 8, that when Met-419 was changed to Ala-419, the optimal acyl donor changed from lauric acid ($C_{12}$) to myristic acid ($C_{14}$), but when Val-649 was changed to Ile-649, the optimal choice of fatty acid remained the same as that of the wild-type.

It is further suggested that M419A might be related mainly to the change in the molecular weight of amino acid side chains that were essential for the catalytic activity of the enzyme (the molecular weights of methionine and alanine are 149 and 89, respectively, and the hydropathy index are 1.9 and 1.8, respectively).

Also, as shown in Table 4, supra, the mutant-type lipases M419A and V649I showed 2.0 and 4.0-fold increases in ester hydrolysis over the wild-type lipase, as demonstrated by their respective catalytic efficiency ($k_{cat}/K_m$). However, the wild-type and V419I mutant had similar catalytic efficiency in the ester synthesis, which indicated that there was little correlation between the ester synthesis and ester hydrolytic activities of the lipases.

Similar studies in other staphylococcal lipases were observed by Talon et al., *Enzyme Microbial. Technology* (1996), 19:620–622, who produced ethyl esters from hexanoic to oleic acids in n-hexane by *S. warneri* and *S. xylosus* lipases. The esterification yields reached an optimum for the decanoic acid. Under their conditions, however, the esterification yield of oleic acid was only half of the decanoic acid.

7. Effect of Acids Structure on the Synthesis of Decyl Esters by the Wild-type and Mutant-type Lipases from *S. epidermidis*

To study the acids structure of acyl donors, the lipase-catalyzed esterification reactions of decyl alcohol with various acids were investigated. As shown in Table 9, the yields of decyl esters where the primary acids were unsaturated acids (e.g., oleic acid, linoleic acid, DHA, but not EPA) were much greater than those of the saturated acids, both catalyzed by the wild-type and the V649I mutant-type lipases. The optimum unsaturated fatty acid for producing decyl esters was oleic acid.

Conversely, in comparison with the wild-type lipase, the M419A mutant-type lipase showed a dramatic decrease in the conversion yield of DHA ester. On the other hand, the *S. epidermidis* lipases (wild-type, M419A, and V649I) could catalyze ester syntheses from decyl alcohol and fatty acids with a primary straight carbon chain but they could not esterify carboxylic acids having aliphatic or aromatic cyclic carbon chains such as cyclohexane-carboxylic acid and benzoic acid (Table 9).

TABLE 9

Effect of Acids Structure on the
Synthesis of Decyl Esters by the S. epidermidis Lipases[a]

| | yield (%)[b] | | |
|---|---|---|---|
| acids | wild type | M419A | V649I |
| stearic acid | 12.11 | 11.69 | 12.11 |
| oleic acid | 65.32 | 62.01 | 58.36 |
| linoleic acid | 43.54 | 10.30 | 38.26 |

TABLE 9-continued

Effect of Acids Structure on the
Synthesis of Decyl Esters by the *S. epidermidis* Lipases[a]

| acids | yield (%)[b] | | |
|---|---|---|---|
| | wild type | M419A | V649I |
| EPA[c] | 6.82 | 3.25 | 6.59 |
| DHA[d] | 49.81 | 0.60 | 25.35 |
| benzoic acid | 0 | 0 | 0 |
| cyclohexane-carboxylic acid | 0 | 0 | 0.12 |

[a]The enzyme (16,500 units) was added to a reaction mixture (1 mL) containing 50 mM fatty acids and 50 mM decyl alcohol in 50 mM phosphate buffer (pH 6.0) and reacted at 33° C. for 10 hours.
[b]The percentage of yield was defined as the molar ratio of the resultant ester to the original reactants.
[c]EPA, eicosapentaenoic acid;
[d]DHA, docosahexaenoic acid.

8. Effects of Chain Length of Primary Alchols on Esterification with Oleic Acid by the Wild-type or Mutant-type Lipases from *S. epidermidis*

The yields of esters catalyzed by the wild-type or mutant-type lipases were affected by the chain-length of different alcohols. As shown in Table 10, the yield of decanoyl oleate was much greater than the longer or shorter chain length alcohols, as catalyzed by the wild-type and M419A mutant enzymes, although the yields of esters catalyzed by the wild-type and M419A mutant enzymes were similar.

As for the V649I mutant-type lipase, the yields of esters when butanol, hexanol, octanol and dodecanol were used were much greater than those of the wild-type and the M419A mutant-type lipases. The V649I mutant-type lipase had much broader alcohol selectivity for ester synthesis. These results indicated that Val-649 might be an essential residue for alcohol-binding in ester synthetic activity.

TABLE 10

Effect of Chain Length of Primary Alcohols on
Esterification with Oleic Acid by the
Recombinant *S. epidermidis* Lipases[a]

| primary alcohol | yield (%)[b] | | |
|---|---|---|---|
| | wild type | M419A | V649I |
| ethanol | 0 | 0 | 0 |
| butanol | 11.13 | 3.1 | 21.29 |
| hexanol | 3.39 | 3.39 | 65.81 |
| octanol | 14.0 | 8.71 | 57.29 |
| decanol | 64.35 | 60.19 | 57.1 |
| dodecanol | 34.35 | 34.35 | 84.19 |
| tetradecahol | 18.39 | 34.35 | 39.68 |
| hexadecanol | 21.19 | 24.19 | 25.35 |

[a]The enzyme (18,600 units) was added to a reaction mixture (1 mL) containing 50 mM oleic acid and 50 mM primary alcohols and reacted at 33° C. for 10 hours.
[b]The percentage of yield was defined as the molar ratio of the resultant ester to the original reactants.

9. Effect of Alcohols Structure on Esterification with Oleic Acid by the Wild-type or Mutant-type Lipases from *S. epidermidis*

To study the effects of alcohols of different carbon chains on the ester synthesis activity, oleic acid was reacted with primary alcohols (1-decanol, geraniol, and oleyl alcohol), secondary alcohols (2-butanol and cyclohexanol), and a tertiary alcohol (tertiary butanol). The results are shown in Table 11. The esterification of primary alcohols had much higher yields than those of secondary and tertiary alcohols by wild-type and mutant enzymes.

TABLE 11

Effect of Alcohol Structures on Esterification with
Oleic Acid by the Recombinant *S. epidermidis* Lipases[a]

| alcohols | | yield (%)[b] | | |
|---|---|---|---|---|
| | | wild type | M419A | V649I |
| primary alcohol | 1-Decanol | 64.35 | 60.19 | 57.1 |
| | geraniol | 38.56 | 14.87 | 75.24 |
| | oleyl alcohol | 37.05 | 24.35 | 43.28 |
| secondary alcohol | 2-butanol | 0 | 0 | 0 |
| | cyclohexanol | 1.69 | 0 | 1.03 |
| tertiary alcohol | tertiary butanol | 0 | 0 | 0 |

[a]The enzyme (18,600 units) was added to a reaction mixture (1 mL) containing 50 mM oleic acid and 50 mM alcohols and reacted at 33° C. for 10 hours.
[b]The percentage of yield was defined as the molar ratio of ester to original reactants.

In addition, in comparison with the amino acid sequences of four other staphylococcal lipases that have been characterized further confirmed that the amino acids sequence of the *S. epidermidis* lipase was similar to *S. hyicus* lipase. The C-terminal regions were closely related, with 43% of the 386 residues being identical and 35% having conservative changes. The results further confirmed the amino acid residues surrounding the Ser-His-Asp active site were important for substrate specificity and enzyme catalytic efficiency.

CONCLUSION

The present invention showed that the recombinant 43-kDa lipase from *S. epidermidis*, with a C-terminal His-tag as well as the mutant-type lipases engineered by site-directed mutations could be easily overexpressed and purified. This success overcame a time-consuming, multi-step purification problem.

The wild-type and mutant-type lipases of *S. epidermidis* were of particular interests because they allowed catalysis of ester synthesis without the uses of organic solvents. They presented the following advantages: (i) avoiding the problem of toxicity and flammability of organic solvents; and (ii) simplification of product purification conditions. Considering the specificity of the enzymes, they could be used to produce esters of different size and length, such as medium-chain esters, geranyl esters and unsaturate esters. The enzymes could be further engineered for the synthesis of short-chain esters and some useful fatty acids.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

What is claimed is:

1. A purified mutant lipase comprising a serine-histidine-aspartic acid catalytic triad; wherein the amino acid residue following said serine residue of said triad is replaced with an alanine; triad wherein said mutant lipase hydrolyzes fatty acid esters or esterifies fatty acids; and wherein the wild-type lipase of said mutant lipase is isolated from a gram positive or gram negative bacterium or fungus.

2. The purified mutant lipase according to claim 1, wherein the last amino acid residue of said mutant lipase is further replaced with a glutamic acid residue and 6 histidine residues are fused to the C-terminus of said glutamic acid residue.

3. The purified mutant lipase according to claim 1, wherein said lipase is a mutant from *staphylococcus*.

4. The purified mutant lipase according to claim 3, wherein said lipase is a mutant lipase from *Staphylococcus epidermidis*.

5. The purified mutant lipase according to claim 1, wherein said lipase further comprises an isoleucine residue following said histidine residue of said triad.

6. The purified mutant lipase according to claim 4, wherein said lipase has the amino acid sequence of SEQ ID NO:15.

7. The purified mutant lipase according to claim 1, wherein said lipase comprises the isoleucine residue following said histidine residue of said triad.

8. The purified mutant lipase according to claim 1, wherein said lipase hydrolyzes fatty acid esters.

9. The purified mutant lipase according to claim 1, wherein said lipase esterifies fatty acids with alcohols.

10. The purified mutant lipase according to claim 1, wherein said lipase esterifies fatty acids without using organic solvents.

11. A method for producing the mutant lipase according to claim 1 or 2, comprising:
  (a) Synthesizing a mutant gene encoding said mutant lipase by a site-directed mutagenesis using polymerase chain reaction (PCR);
  (b) Ligating said mutant gene to a plasmid;
  (c) transfecting said ligated plasmid into a host cell; and
  (d) Culturing said host cell to overexpress said lipase.

12. The method according to claim 11, wherein said site-directed mutagenesis uses an oligonucleotide primer of SEQ ID NO: 1 corresponding to the N-terminal, an oligonucleotide primer of SEQ ID NO: 2 corresponding to the C-terminal and a mutagenic primer of SEQ ID NO: 6 to produce said mutant gene encoding said mutant lipase which contains said alanine residue following said serine residue of said triad.

13. The method according to claim 11, wherein said mutant gene is digested with restriction endonucleases before ligated to said plasmid.

14. The method according to claim 11, wherein said plasmid is pET-20(b)$^+$.

15. The method according to claim 11, wherein said host cell is a prokaryotic cell.

16. The method according to claim 15, wherein said prokaryotic cell is *Escherichia coil*.

17. The method according to claim 11, wherein said over expressed lipase is further purified by a $NiSO_4$– charged His-bind resin column.

18. A method for enhancing flavor in food comprising:
  (a) Enzymatically synthesizing a flavor ester from alcohol and fatty acid by the lipase according to claim 5; and
  (b) Adding said flavor ester to food.

19. The method according to claim 18, wherein said alcohol is a primary alcohol having carbon chain length of $C_2$–$C_{16}$.

20. The method according to claim 18, wherein said flavor ester is decyl myristate or decyl oleate.

21. A method for enhancing flavor in food comprising:
  (a) Enzymatically synthesizing a flavor ester from alcohol and fatty acid by the lipase according to claim 7; and
  (b) Adding said flavor ester to said food.

22. The method according to claim 21, wherein said alcohol is a primary alcohol having carbon-chain length of $C_2$ to $C_{12}$.

23. The method according to claim 20, wherein said flavor ester is decyl laurate.

24. The purified mutant lipase according to claim 1, wherein said gram positive bacterium is one selected from the group consisting of *Staphylococcus epidermidis, Staphylococcus hyicus, Staphylococcus aureus, Bacillus thermocatenularus, Staphylococcus xylosus,* and *Staphylococcus warneri*.

25. The purified mutant lipase according to claim 1, wherein said gram negative bacterium is one selected from the group consisting of *Acinetobacter calcoaceticus, Arthrobacter sp., Pseudomonas aeruginosa, Pseudomonas cepacia, Pseudomonas vulgaris,* and *Serratia marcescens*.

26. The purified mutant lipase according to claim 1, wherein said fungus is one selected from the group consisting of *Humicola lanuginose, Candida cylindracea,* and *Rhizopus oryzae*.

27. A purified mutant lipase comprising a serine-histidine-aspartic acid catalytic triad; wherein the amino acid residue following said histindine residue of said triad is replaced with an isoleucine, wherein said mutant lipase hydrolyzes fatty acid esters or esterifies fatty acids; and wherein the wild-type lipase of said mutant lipase is isolated from *staphylococcus*.

28. A purified mutant lipase having the amino acid sequence of SEQ ID NO:17.

* * * * *